United States Patent [19]

Gurney

[11] 4,403,961
[45] Sep. 13, 1983

[54] METHOD AND APPARATUS FOR FABRICATING DENTAL PROSTHETICS

[76] Inventor: John I. Gurney, 2921 Weathervane, Dallas, Tex. 75228

[21] Appl. No.: 339,004

[22] Filed: Jan. 12, 1982

[51] Int. Cl.³ ................................................ A61C 9/00
[52] U.S. Cl. ...................................... 433/213; 433/51
[58] Field of Search ........................ 433/76, 6, 51, 213

[56] References Cited

U.S. PATENT DOCUMENTS 2,467,432  4/1949  Keshling .............................. 433/6
3,100,344  8/1963  Sharp ................................. 433/76

Primary Examiner—Robert Peshock
Attorney, Agent, or Firm—Harold E. Meier

[57] ABSTRACT

A method for fabricating three directional dental prosthetics. A wax setup of the patient's arches containing artificial dentures is prepared. The wax setup is tried in the patient's mouth to determine centric occlusion. A matrix of the setup is prepared when the centric occlusion is satisfactory. A setup of pumice teeth is then prepared by pouring a pumice compound into the matrix and allowing the compound to harden. A duplicate setup containing pumice teeth is prepared by transferring the pumice teeth onto duplicate models of the patient's upper and lower arches. The duplicate setup is then mounted in the patient's mouth and incisal-occlusal surfaces corresponding to the patient's natural mandibular movement are abrasively milled on the pumice teeth by exercising the duplicate setup in the patient's mouth. Incisal-occlusal surfaces milled in the pumice teeth are then mechanically reproduced on artificial dentures in the wax setup from the duplicate setup on a mill-in-jig.

5 Claims, 10 Drawing Figures

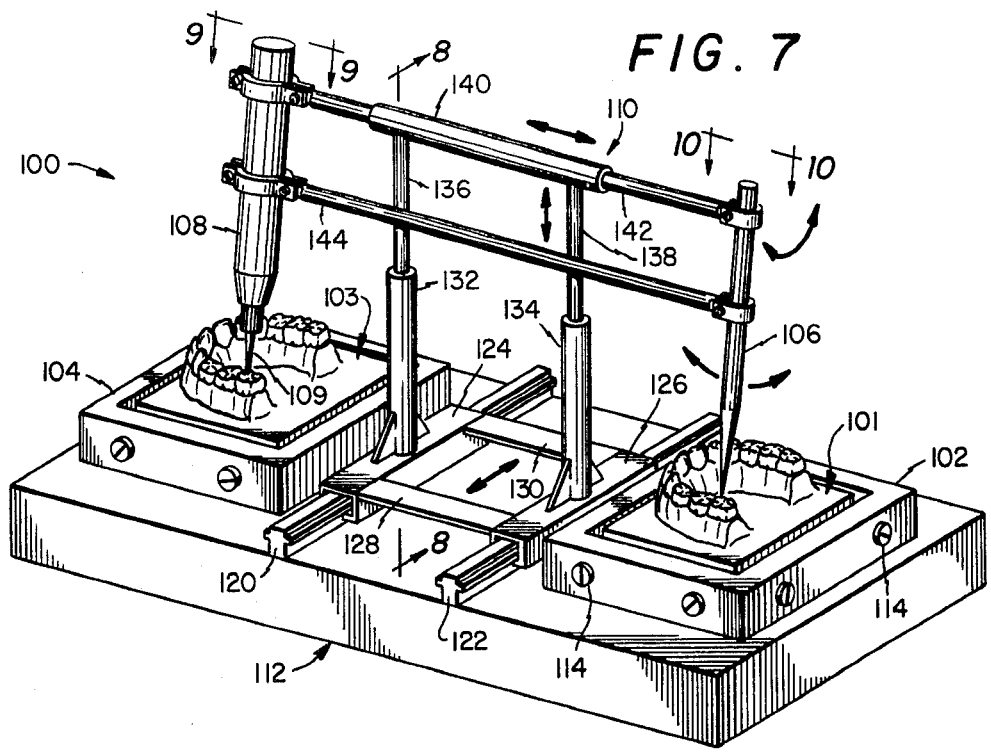
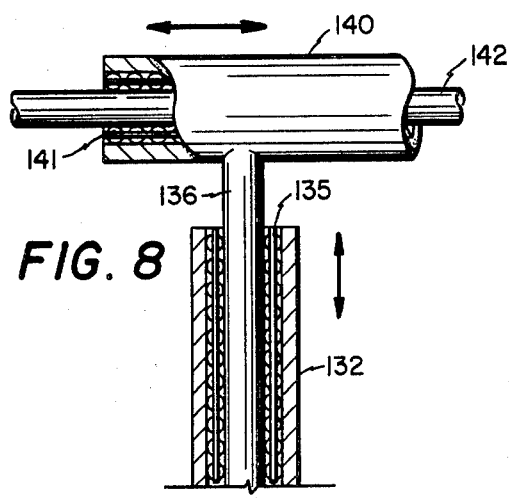
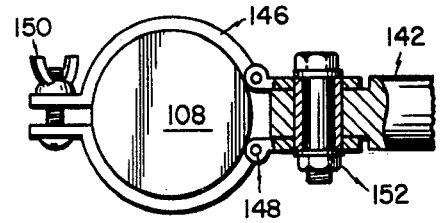
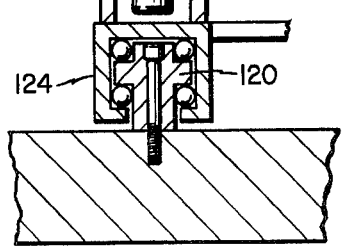

METHOD AND APPARATUS FOR FABRICATING DENTAL PROSTHETICS

TECHNICAL FIELD

The invention pertains to fixed and removable dental restorations and more particularly to a method and apparatus for fabricating three directional dental prosthetics.

BACKGROUND ART

Conventional dental prosthetics are constructed to accommodate the up and down mandibular movement of the jaw with only limited regard to movement of the jaw in the protrusive and lateral directions. Such appliances may have good occlusal relationship in centric, but may result in complications due to interfering teeth which are not built to conform to the patient's natural mandibular movement.

Techniques for making three directional appliances are known in the art, but are costly, complex and time consuming. One such technique involves the use of a simulator which attempts to duplicate the three dimensional jaw movements of the patient outside of the mouth. This technique is time consuming because it requires the dentist to take a series of bites in the mouth and to make tracings of the patient's mandibular movements. To be successful, the bites and tracings must be taken with great accuracy.

This procedure is extremely time consuming and very expensive, not only in chair time in the dentist's office, but in fabrication time in the laboratory. Accordingly, a simpler method and apparatus is needed to reduce the costs and time required for fabricating three directional prosthetics.

DISCLOSURE OF THE INVENTION

The present invention provides a simplified method for fabricating both removable and fixed dental restorations that accommodate three directional movement with a minimum of chair time and fabrication time.

According to one aspect of the invention, a wax setup of the patient's arch containing artificial teeth is prepared. The wax setup is tried in the patient's mouth to determine centric occlusion. If the centric occlusion is satisfactory, an impression of the setup is made and a pumice compound is poured into the impression and allowed to harden to form a set of pumice teeth. The pumice teeth are then transferred onto duplicate models of the upper and lower arches to create a duplicate setup. The duplicate setup is mounted in the patient's mouth and the patient exercises the setup through the entire range of mandibular movements to abrate the pumice teeth into three directional occlusion. The duplicate setup containing the pumice teeth is then removed from the patient's mouth and mounted on a mill-in-jig in alignment with the wax setup. The occlusal-incisal surfaces formed on the duplicate setup in accordance with the patient's natural jaw movements are then mechanically ground on the artificial teeth in the wax setup.

In accordance with yet another aspect of the present invention, an apparatus for reproducing the occlusal-incisal surfaces from a duplicate setup onto a master setup is disclosed. The apparatus comprises a platform having a first retaining means for retaining a duplicate setup containing pumice teeth in fixed position and a second retaining means for retaining a master setup in fixed position both in vertical and horizontal alignment with each other with the duplicate setup. A stylus member disposed generally perpendicular to the platform is mechanically connected to the platform, but capable of three directional and rotational movement. A turbine handpiece containing a bit is axially disposed generally perpendicular to the platform proximate the first retaining means. The turbine handpiece is mechanically connected to the stylus by a pantographic linkage whereby the movement of the stylus is duplicated by the handpiece such that the occlusal-incisal surfaces on the secondary setup are ground into the master setup when the stylus passes over the surfaces of the duplicate setup.

BRIEF DESCRIPTION OF THE DRAWINGS

A more complete understanding of the invention can be had by reference to the following Detailed Description in conjunction with the accompanying Drawings, wherein:

FIG. 7 is a perspective view of the mill-in-jig used in one step of the present invention;

FIG. 8 is a partial section view of the pantographic linkage of FIG. 7;

FIG. 9 is a section view of one of the clamps shown in FIG. 7; and

FIG. 10 is a section view of the other of the clamps shown in FIG. 8.

DETAILED DESCRIPTION

The present invention is aimed at improving and simplifying the conventional methods of fabricating three directional dentures or fixed bridges. Three directional prosthetics are designed to afford the patient maximum efficiency in mastication by performing as nearly as possible according to the patient's natural jaw movements, unlike standard dentures which are built only to accommodate the up and down mandibular movement.

As is conventional in most methods of making dentures, an impression of the patient's upper and/or lower arches is made in alginate or other rubber base material. A cast or model of the upper and lower ridges is then made. A conventional stone gypsum product is prepared and poured into the impression. This product sets up to form a master model of the patient's upper and lower arches. A duplicate model is then made by taking an impression of the cast or model in a standard hydrocolloid impression material such as PER-FLEX manufactured by Nobillium. The stone gypsum product is prepared, poured into the hydrocolloid impression material, and allowed to set up to form a duplicate model of the upper and lower arches.

After the master and duplicate models of the patient's upper and/or lower ridges have been fabricated, base plates are formed for each model. The procedure for forming base plates is entirely conventional and consists of applying an acrylic resin or shellac over the master and duplicate models. After this material hardens, it is removed from the models. The base plates with occlusal rims are then used to take the patient's "bite" to determine the centric registration.

Figure 1:
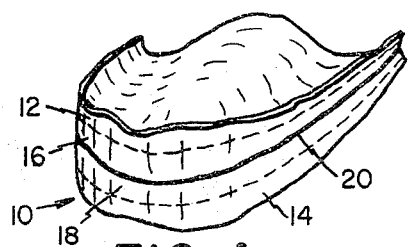
FIG. 1 is a perspective view of the upper and lower base plates containing occlusal rims formed thereon for use in taking the patient's bite in one step of the invention.

FIG. 1 illustrates a "bite" 10, which is taken in the patient's mouth for a full-full upper and lower restoration. Where only a full upper or full lower restoration is desired, then only an upper or lower bite is required. Upper and lower base plates 12 and 14, formed as previously described, are fitted with occlusal rims 16 and 18 made of relatively hard wax and formed on the rim of each base plate. Rims 16 and 18 extend from the base plates 12 and 14 to the occlusal plane 20. The patient's centric registration is determined by placing both the base plates in the patient's mouth and forcing the occlusal rims together into a bite when the patient bites down. Alternatively, a face bow or tracings could be employed to arrive at the patient's hinge axis and centric registration.

Figure 4:
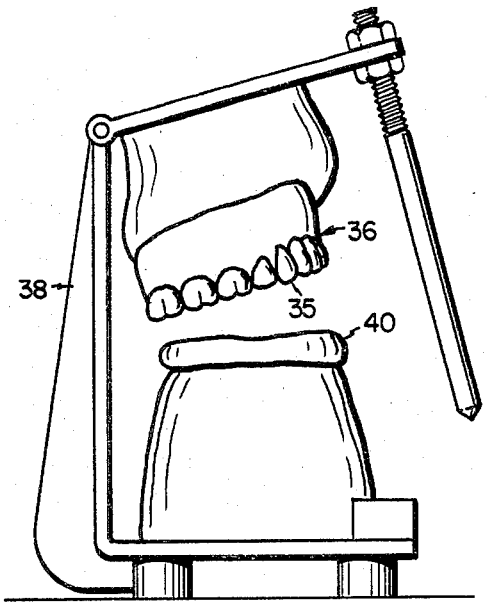
FIG. 4 illustrates the use of a master setup in a straight line articulator to form a duplicate setup.
Figure 5:
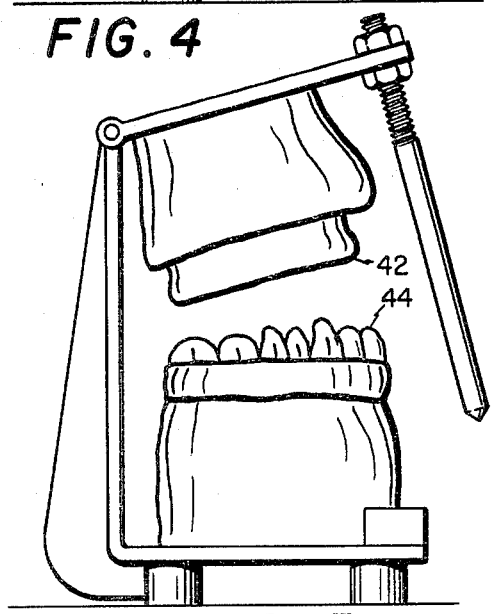
FIG. 5 illustrates the formation of a duplicate setup in a straight line articulator.
Figure 6:
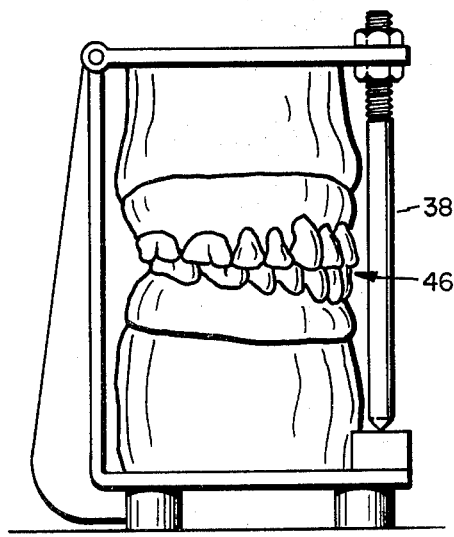
FIG. 6 illustrates the centric registration obtained in the duplicate setup.

After the bite is taken, it is mounted in a conventional straight line articulator of the type shown in FIG. 4, 5 or 6. This articulator preserves the occlusion between the models and permits a three directional denture to be fabricated in accordance with the steps hereafter described.

In the next step, a wax (master) setup is done in centric. Artificial teeth are set into wax disposed on the base plates 16, 18 by applying heat and forcing them into the wax. After completing the master setup, the patient makes a subsequent visit to the dentist where the setup is tried in the patient's mouth to check the centric occlusion. If the centric occlusion is unsatisfactory, a new "bite" is taken, a new wax setup is made and the procedures described above are repeated.

Figure 2:
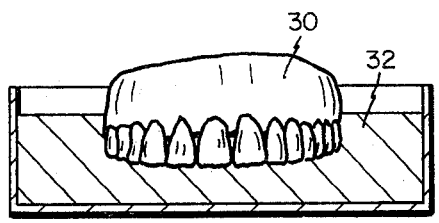
FIG. 2 illustrates the formation of an impression from the master setup for use in one step of the invention.
Figure 3:
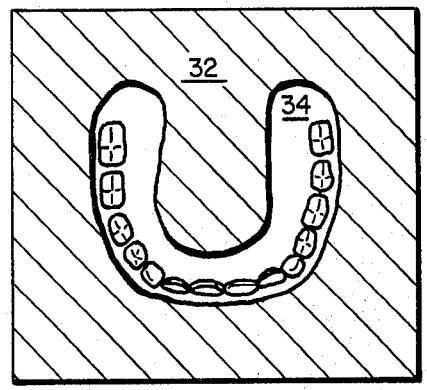
FIG. 3 illustrates the impression formed by the procedure illustrated in FIG. 2.

If the centric occlusion of the wax setup is found to be satisfactory, an impression of the teeth in the setup is made. FIG. 2 illustrates this process. The wax setup 30 is impressed into a hydrocolloid material 32 slightly past the cervical portion of the teeth to form an impression 34 (FIG. 3). When the material 32 hardens, a pumice compound is poured into the impression 34 (FIG. 3) to make a set of "pumice teeth" 35 for each of the upper and lower arches, in the case of a full-full setup, or in the case of just edentulous upper or lower arches, only one set of pumice teeth for the edentulous arch of portion thereof. A suitable pumice compound for use in this process would be a mixture of die stone, such as VEL MIX, water and a fine flour polishing pumice.

When the pumice teeth 35 harden in impression 34, they are then transferred onto the duplicate models. The upper or lower arch model 36 with the pumice teeth 35 is mounted in the articulator 38 as shown in FIG. 4. The articulator is closed, the setup is impressed into a plaster patty 40 and allowed to harden into a matrix. When the matrix formed in the plaster patty 40 hardens, the articulator 38 is opened, the master setup is removed and the pumice teeth are then seated into the matrix. The process may be repeated for the corresponding arch.

Referring now to FIG. 5, the prepared base plates for the upper and lower duplicate models are now placed on the models in articulator 38. An acrylic, such as FAST CURE, is now applied onto the model 36 of the upper or lower arch and the articulator is closed, bringing the pumice teeth 35 into registration with the duplicate model 36. Excess acrylic is trimmed away leaving just enough acrylic to secure the teeth from moving while being exercised in the mouth. When the acrylic hardens, the duplicate setup is removed from the articulator and a veneer of wax is applied over the acrylic to create gingiva. The process is repeated for the corresponding arch. FIG. 6 shows a finished duplicate setup 42 in the articulator with both the upper and lower arches.

At this point, the duplicate setup 42 with the pumice teeth is mounted in the mouth of the patient. Gross occlusal interference on the pumice teeth may be etched away first by the dentist. The patient then exercises the setup in the mouth throughout the full range of mandibular movement until the desirable occlusion is reached. When the natural occlusion has been created, the duplicate setup is removed and sent back to the lab where the natural occlusal surfaces are milled in on the master setup by a pantographic mill-in-jig 100 (FIG. 7).

At the laboratory, the duplicate and master setups are mounted on the mill-in-jig 100 as shown in FIG. 7. The duplicate setup 101 is mounted on the stylus platform 102 and the master setup 103 is mounted on the workpiece platform 104. Both the master and duplicate setups 101, 103 are secured in alignment. The master and secondary setups mounted on platforms 102 and 104 are aligned such that diamond bur 109 and stylus 106 touch corresponding surfaces on the master and duplicate setups. The natural occlusal-incisal surfaces on the pumice teeth are then traced out with stylus 106 and ground on the master setup by a turbine powered handpiece 108 containing a diamond bur 109 by means of a pantographic linkage 110 which reproduces the movements of the stylus in the handpiece. When the natural occlusal-incisal surfaces have been milled in on jig 100, the master setup 103 is further processed by replacing the wax with acrylic and is delivered to the dentist for fitting. The foregoing method also has application to removable partial dentures or single upper or lower dentures.

The same method also has application to fixed crown and bridge restorations. For example, in a single unit crown restoration, preparation work is first completed in the mouth. A master and two duplicate models extending to the patient's full arch are made. A metal or porcelain crown is made in the conventional manner with the height of the cusps allowed to follow the existing dentition. Prospective interferences occurring in the lateral or protrusive movement need not be eliminated. An impression of the crown is then made, as in FIGS. 2 and 3, and a pumice crown reproduction is then made from the impression. The crown is then seated on the master model and mounted on the articulator. A matrix of the crown is made as shown in FIG. 4 to permit the pumice crown to be transferred to one of the duplicate models. On one of the duplicate models, a temporary, removable acrylic partial, overlaying the occlusal surface of the die or prepared tooth, is made with a thin layer of acrylic. The crown is removed from the master model and the acrylic partial is mounted thereto. The pumice crown is then seated into the matrix, the articulator is closed and excess from the pumice tooth is removed from the underside of the crown until the articulator closes completely. The pumice crown is then fastened to the partial with a fast cure acrylic and a veneer of the wax is placed around the joint of the pumice crown and the partial. This appliance is then placed in the patient's mouth and exercised through the full range of mandibular movements. After removal from the patient's mouth, the appliance is seated back on the master model, the pumice crown is seated in the partial on the other duplicate model and aligned on the mill-in-jig to permit the occlusal surfaces on the pumice crown to be ground into the crown. Of course, this technique has application to any restoration of the occlusal surfaces, such as, for example, multiple unit crown and bridge restorations or overlays, et cetera.

Referring now to FIG. 7, the mill-in-jig 100 will be described. As shown in FIG. 7, jig 100 comprises a base plate 112, which supports a stylus platform 102 and a workpiece platform 104. Platforms 102 and 104 are provided with set screws 114 whereby the secondary setup containing the pumice teeth and the master setup can be placed in an alignment. Stylus 106, normally suspended above platform 104, is capable of tracing out any point on the surface of the secondary setup mounted below. Workpiece platform 104, likewise normally suspended above platform 104, is pantographically connected to stylus 106 by linkage 110 and reproduces the tracings of stylus 106 on the master setup mounted to the platform.

Pantographic linkage 110 is capable of reproducing all of the movements of the stylus in the handpiece. A pair of parallel tracks 120 and 122 are provided on base plate 112 which permits perpendicular lateral movement of linkage 110 along the tracks. As best seen in FIG. 7, a pair of guides 124, 126 connected by parallel members 128, 130 form a platform for supporting two upstanding cylindrical support members 132 and 134 to facilitate vertical motion of the linkage. As shown in FIG. 8, support members 132 and 134 contain bearings 135 disposed about rods 136 or 138 to facilitate vertical movement of the rods within the cylinder.

As seen in FIGS. 7 and 8, rods 136 and 138 are rigidly connected to a cylindrical sleeve member 140, which facilitates longitudinal motion in the direction as shown by the arrows. Like support members 132 and 134, sleeve member 140 contains bearings 141 therein adapted to facilitate longitudinal and rotational movement of rod 142 along or about the axis of rotation. A longitudinal second support member 144 is thus likewise provided, parallel to rod 142, to maintain the relationship between the stylus 106 and the handpiece 108 adjacent the platform.

As shown in FIGS. 9 and 10, rods 142 and 144 are connected to handpiece 108 and stylus 106 by clamp member 146 and sleeve 154, respectively. Clamp member 146 and sleeve 154 are vertically hinged at 152 and 156 to facilitate angular movement of stylus 106 and handpiece 108. Clamp 146 is hinged at pins 148 such that it can be opened to enclose handpiece 108. A thumb screw 150 is provided to hand tighten clamp 146 about handpiece 108 to facilitate adjustment of the linkage 110.

Although a single embodiment of the invention has been illustrated in the accompanying Drawings and described in the foregoing Detailed Description, it will be understood that the invention is not limited to the embodiment disclosed, but is capable of numerous rearrangements, modifications and substitutions of parts and elements without departing from the spirit of the invention.

I claim:

1. A method for fabricating three directional dental prosthetics comprising the steps of:
   (1) preparing a wax setup containing artificial dentures of the patient's arches;
   (2) trying the wax setup prepared in step (1) in the patient's mouth to determine centric occlusion;
   (3) making a matrix of the setup prepared in step 1 when the result in step (2) is satisfactory;
   (4) preparing a set of pumice teeth by pouring a pumice compound into the matrix formed in step (3) and allowing said compound to harden;
   (5) preparing a duplicate setup containing pumice teeth by transferring the pumice teeth prepared in step (4) onto duplicate models of the patient's upper or lower arches;
   (6) mounting the duplicate setup prepared in step 5 in the patient's mouth;
   (7) abrasively milling incisal-occlusal surfaces in the pumice teeth corresponding to the patient's natural mandibular movements by exercising the duplicate setup containing pumice teeth in the patient's mouth; and
   (8) mechanically reproducing the incisal-occlusal surfaces of said pumice teeth on said artificial dentures in said wax setup from said duplicate setup.

2. The method of claim 1 wherein said pumice compound prepared in step (4) comprises a mixture of die stone, water and fine flour polishing pumice.

3. The method of claim 1 wherein the occlusal-incisal surfaces of said duplicate setup are mechanically reproduced in step (8) on said master setup by a mill-in-jig.

4. A method for fabricating three directional dental prosthetics comprising the steps of:
   (1) preparing an impression of the patient's upper or lower arches;
   (2) preparing a master model of the patient's upper or lower arches by pouring a hardening material into said impression and allowing said material to set up;
   (3) taking an impression of one or more of said master models in hydrocolloid impression material;
   (4) preparing duplicate models of the patient's upper or lower arches from one or more of the impressions prepared in step (3) by pouring a hardening material into said impression and allowing said material to set up;
   (5) preparing base plates for each of said master and duplicate models prepared in steps (2) and (4) by applying a plastic material over each of said models;
   (6) removing the base plates from each of the models prepared in step (5);
   (7) applying a layer of relatively hard wax extending to the occlusal plane to the top of each of the master base plates as prepared in step (5) to form an occlusal rim on each of said base plates;
   (8) obtaining a bite to determine centric registration by mounting the base plates in the patient's mouth and causing the patient to force the occlusal rims of the upper and lower arches together;
   (9) mounting the bite obtained in step (8) into a straight line articulator;
   (10) removing the models from the master base plates in the articulator in step (9);
   (11) preparing a master setup by setting the artificial dentures in wax on one or more of the base plates in the articulator;

(12) trying the wax setup prepared in step (11) in the patient's mouth to determine centric registration;

(13) making a matrix of the setup prepared in step (11) when the result in step (12) is satisfactory;

(14) preparing a set of pumice teeth by pouring the pumice compound into the matrix formed in step (13) and allowing said compound to harden;

(15) preparing a secondary set containing pumice teeth by transferring the pumice teeth prepared in step (14) on duplicate models of the patient's upper or lower arches;

(16) mounting the secondary setup prepared in step (15) in the patient's mouth;

(17) abrasively milling incisal-occlusal surfaces on the pumice teeth corresponding to the patient's natural mandibular movements by exercising the secondary setup containing the pumice teeth in the patient's mouth; and

(18) reproducing the incisal-occlusal surfaces on the wax setup corresponding to the incisal-occlusal surface on the pumice teeth by mounting said master and secondary setups on the mill-in-jig and reproducing the surfaces of said pumice teeth on said artificial dentures.

5. A method for fabricating fixed crown and bridge restorations comprising the steps of:

(1) preparing the teeth in the patient's mouth for restoration;

(2) preparing a master and two duplicate models of the full arch containing the teeth to be restored;

(3) preparing a crown and bridgework adapted to fit in the patient's mouth as prepared in step (1);

(4) making an impression of the crown and bridge work prepared in step (3);

(5) preparing a pumice reproduction of the crown and bridgework prepared in step (2) by pouring a pumice compound into the impression made in step (4);

(6) preparing acrylic partials overlaying the occlusal surface of the prepared tooth on one of said duplicate models;

(7) mounting the pumice reproduction into said acrylic partials prepared in step (6);

(8) abrasively milling incisal-occlusal surfaces in the pumice reproduction corresponding to the patient's natural mandibular movements by exercising the appliance resulting from step (7) in the patient's mouth; and (9) mechanically reproducing the incisal-occlusal surfaces on said pumice reproduction on said crown and bridgework.

* * * * *